(12) United States Patent
Van Baelen et al.

(10) Patent No.: US 8,626,307 B2
(45) Date of Patent: Jan. 7, 2014

(54) INTEGRATED CIRCUIT CONFIGURATION

(75) Inventors: Erika J. Van Baelen, Heverlee (BE); Jan Janssen, St. Ives (AU); Tony M. Nygard, Terrigal (AU); Koen Van den Heuvel, Hove (BE)

(73) Assignee: Cochlear Limited, Macquarie University, NSW (AU)

( * ) Notice: Subject to any disclaimer, the term of this patent is extended or adjusted under 35 U.S.C. 154(b) by 371 days.

(21) Appl. No.: 12/934,912

(22) PCT Filed: Mar. 25, 2009

(86) PCT No.: PCT/AU2009/000336
§ 371 (c)(1),
(2), (4) Date: Dec. 23, 2010

(87) PCT Pub. No.: WO2009/117767
PCT Pub. Date: Oct. 1, 2009

(65) Prior Publication Data
US 2011/0087325 A1    Apr. 14, 2011

(30) Foreign Application Priority Data
Mar. 25, 2008  (AU) ................................ 2008901434

(51) Int. Cl.
*A61N 1/00* (2006.01)
(52) U.S. Cl.
USPC ........................................................ 607/55
(58) Field of Classification Search
USPC ........................................................ 607/55
See application file for complete search history.

(56) References Cited

U.S. PATENT DOCUMENTS

| | | | |
|---|---|---|---|
| 4,532,930 A * | 8/1985 | Crosby et al. | 607/57 |
| 5,336,951 A | 8/1994 | Josephson et al. | |
| 5,522,865 A | 6/1996 | Schulman et al. | |
| 5,608,341 A | 3/1997 | Andersson | |
| 5,629,635 A | 5/1997 | Reno | |
| 6,938,235 B2 * | 8/2005 | Breejen et al. | 326/38 |
| 7,085,870 B2 * | 8/2006 | Do | 710/302 |
| 7,539,967 B1 * | 5/2009 | Orthner et al. | 716/138 |
| 2005/0113884 A1 | 5/2005 | De Paep | |

OTHER PUBLICATIONS

Extended European Search Report for European Application No. 09725346.2 mailed Sep. 4, 2012 (7 pages).
Analog Devices® ADMC331, "Single Chip DSP Motor Controller", 2000.
International Search Report, International Application No. PCT/AU2009/000336, filed on Mar. 25, 2009, mailed Jul. 1, 2009.
Microchip Technology Inc., "Bootloader for dsPIC30F/33F and PIC24F/24H Devices", 2007.

* cited by examiner

*Primary Examiner* — Christopher D Koharski
*Assistant Examiner* — Michael Carey
(74) *Attorney, Agent, or Firm* — Kilpatrick, Townsend & Stockton, LLP.

(57) ABSTRACT

An electronic system is provided which includes a number of components. Each component includes one or more integrated circuits. During normal operation of the system, each integrated circuit provides individual operating functionality for its respective component. At least one of the integrated circuits is installed as a generic integrated circuit capable of providing any one of a number of potential operating functionalities. The generic integrated circuit is arranged to determine where in the system it has been installed upon system initialization, and, based upon the determination, configure itself to provide the required individual operating functionality for normal operation of the system.

19 Claims, 3 Drawing Sheets

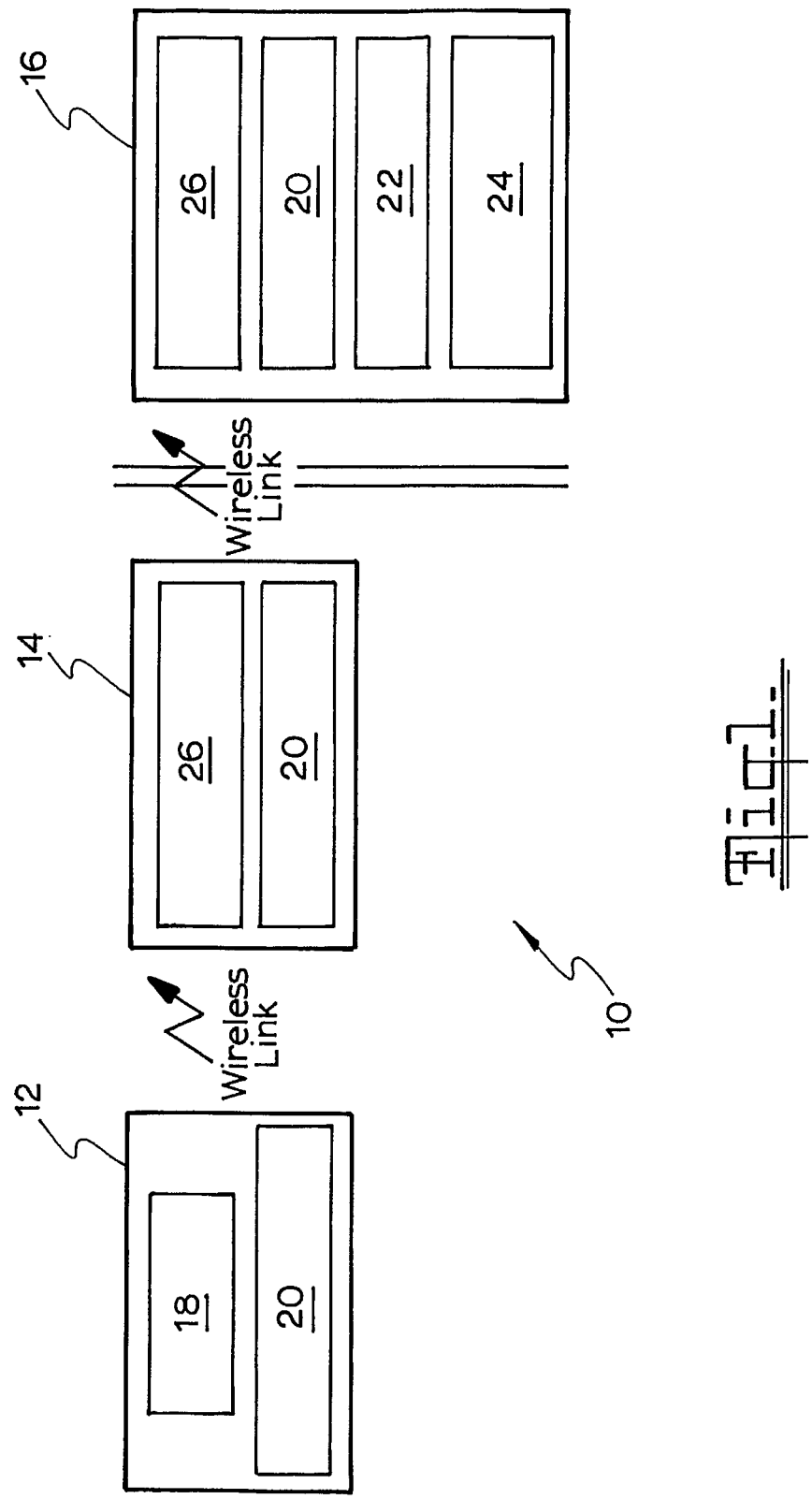

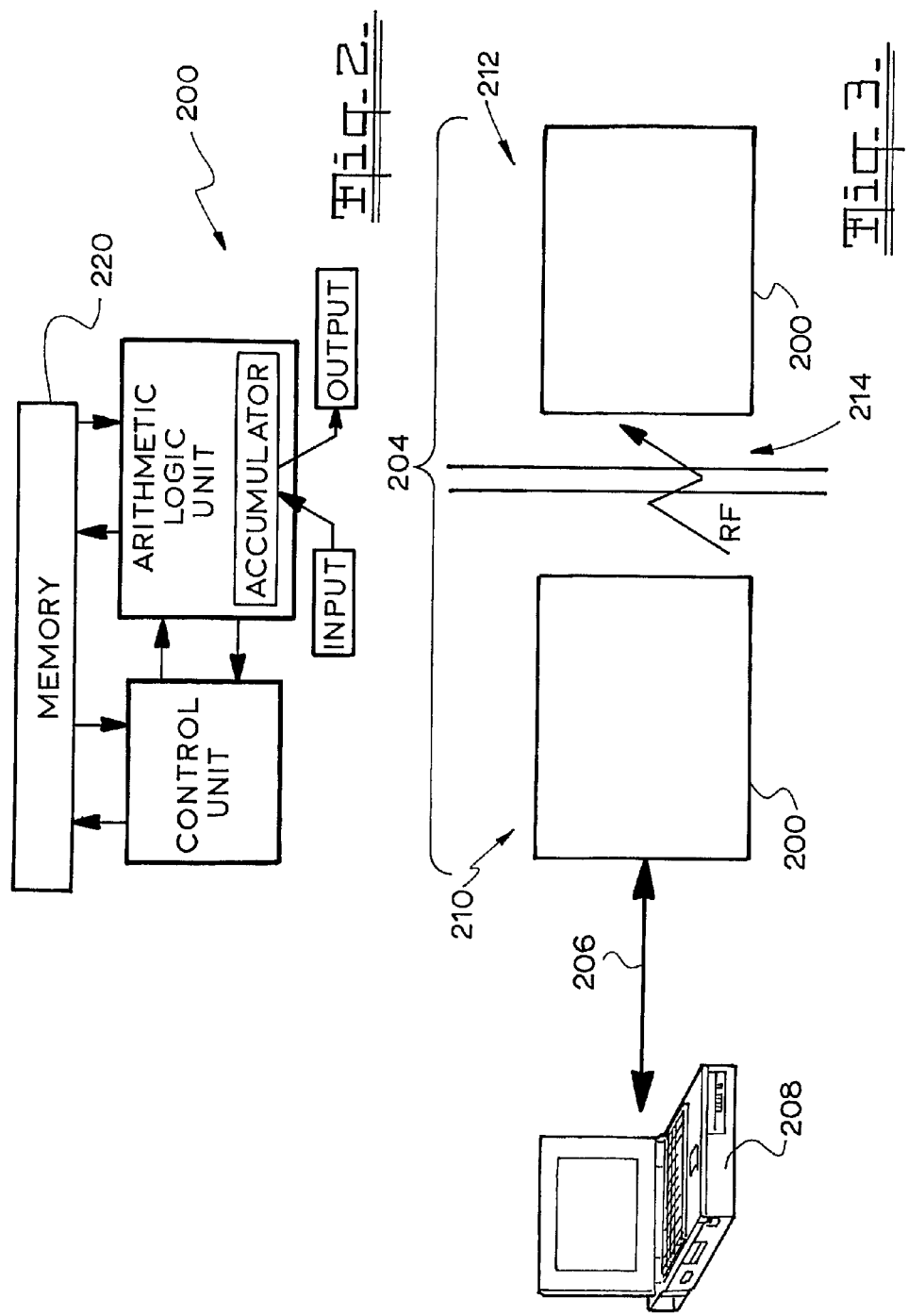

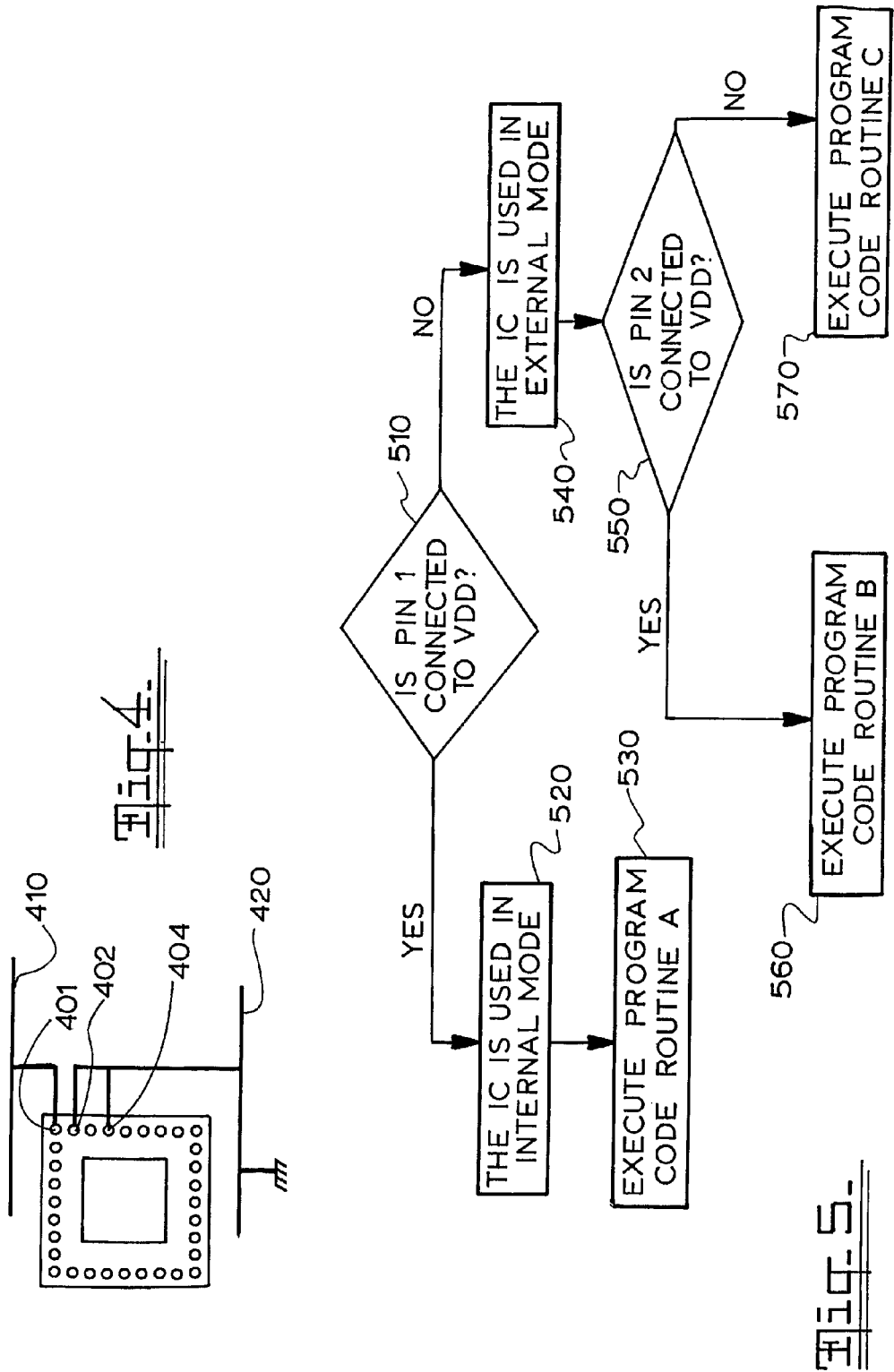

INTEGRATED CIRCUIT CONFIGURATION

CROSS-REFERENCE TO RELATED APPLICATION

The present application is a National Stage application of PCT/AU2009/000336 entitled "Electronic Component Configuration", filed on Mar. 25, 2009, which claims priority from Australian Provisional Patent Application No. 2008901434, filed on Mar. 25, 2008, which are hereby incorporated by reference herein.

BACKGROUND

1. Field of the Invention

The present invention relates to complex electronic devices, for example medical prosthesis systems.

2. Related Art

Complex electronic devices can incorporate many integrated circuits (ICs) which each provide different functionalities which cooperate to provide a working system.

Particular examples of complex electronic devices are complex medical devices, for example implantable hearing systems. An implantable hearing system typically consists of an external part and an internal part (i.e. the so-called implant). External and internal parts communicate with each other using a wireless link through the skin. Both internal and external parts can consist of one or multiple components, for example:

- An external sound processor, capturing the microphone signal and conditioning the signal before sending it to the implant, is a typical component of the external part. Other external components could be a remote control, a programming interface, a diagnostics device, etc.;
- The internal part typically has a stimulator component that is responsible for stimulating the auditory nerve. Internal components also can include an implantable battery, implantable microphone, a receiver for a wireless link, etc.

Each of these components operates according to its own functional requirements. The cooperation of these individual functionalities provides a complex system which together provides the normal working operation of the system.

Continued developments in hearing devices are driven by market demands. Some demands relate to better signal processing to offer more hearing performance. Other demands include additional functionality to make the device more user friendly, for example an enhanced user interface, and connectivity to a PC or to wireless equipment.

When facing developments related to enhanced signal processing and functionality two challenging problems need to be resolved:

- Miniaturization so that everything fits in as small a volume as possible, and
- Low power consumption to achieve an acceptable battery life.

It is proposed that both challenges can be met by including integrated circuits (ICs) in the system. Hence there is an expected future trend towards the incorporation of more ICs within the same system. Multiple ICs like microcontrollers or Digital Signal Processors (DSPs) (but also other ICs like wireless transceivers) are expected to be used more widely within the one implantable hearing system.

However, there are a number of disadvantages when using ICs for implantable hearing devices because they require a collective number of very specific functionalities that are not found in other devices on the market.

The specific functionalities for implantable hearing devices often require that custom-made ICs are used (i.e. application specific ICs or ASICs) and installed in the device during manufacture. Design, verification and qualification of such custom-made ICs for medical implantable devices is expensive and time-consuming. Therefore, to follow the trend of installing an increased number of custom-made ICs into a hearing device system results in a marked increase in the cost of manufacture.

SUMMARY

In one aspect of the present invention, there is provided, an electronic system including a plurality of components, each component including one or more integrated circuits, wherein each integrated circuit is, during normal operation of said system, configured to provide individual operating functionality for its respective component; wherein at least one of said integrated circuits is configured to be installed as a generic integrated circuit capable of providing any one of a number of potential operating functionalities, said generic integrated circuit being configured to determine where in said system it has been installed upon system initialization by determining which of its connecting pins have been electrically connected during installation, and, based upon said determination, configure itself to provide the required individual operating functionality for normal operation of said system.

In another aspect, there is provided a method for configuring the operating functionality of an electronic system, said system including a plurality of components, each component including one or more integrated circuits, wherein, during normal operation of said system, each integrated circuit provides individual operating functionality for its respective component; said method comprising: installing at least one of said integrated circuits as a generic integrated circuit capable of providing any one of a number of potential operating functionalities, determining, by said generic integrated circuit, where in said system the generic integrated circuit been installed; and based upon said determination, said generic integrated circuit configuring itself to provide the required individual operating functionality for normal operation of said system.

BRIEF DESCRIPTION OF THE DRAWINGS

Embodiments of the present invention will now be described with reference to the accompanying drawings, in which:

FIG. 1 illustrates a block diagram of an example of an implantable hearing prosthesis system;

FIG. 2 illustrates an example of a processor IC architecture;

FIG. 3 illustrates another implantable hearing system example;

FIG. 4 illustrates an electrical connection of an IC;

FIG. 5 shows an example flowchart of the boot loader program execution.

DETAILED DESCRIPTION

In a broad form, embodiments of the present invention provide a construction in which a common IC can be used for a variety of functions, with the IC itself determining which function and hence which parts of firmware or software to enable or load based on the position of the IC in the configuration.

As will be discussed further below, in an embodiment, upon system initialization, the generic integrated circuit (also referred to herein as a common IC) executes an initialization program that allows the generic integrated circuit to detect where in a system the generic integrated circuit has been installed. The generic integrated circuit determines where in the system it has been installed by determining which of its connecting pins have been electrically connected during installation. Upon determining where in the system it has been installed, the generic integrated circuit downloads a required operating program from an external source, the required operating program, upon execution by the generic integrated circuit, providing the required individual operating functionality for the integrated circuit.

Embodiments of the present invention may advantageously employ the use of one or more generic integrated circuits capable of providing any one of a number of required functionalities installed during manufacture the system. Upon system initialization, each generic integrated circuit configures itself to its actual required functionality on the basis of where it has been installed within the system. Hence, specific IC customization in advance is not a prerequisite of manufacture, and hence costs can be reduced.

Embodiments of the present invention will be described with reference to particular illustrative examples. However, it will be appreciated that embodiments of the present invention are applicable to any electronic system which uses multiple ICs. While the following description pertains to an implantable hearing prosthesis system, the present invention may be applied with any suitable hearing prosthesis system, for example a hybrid electrical/acoustic system, a cochlear implant system, an implantable hearing aid system, a middle ear stimulator or any other suitable hearing prosthesis. It may be applied to a system with totally implanted components, or to a system which additionally includes one or more external components. It will be appreciated that the present implementation is described for illustrative purposes, and its features are not intended to be limitative of the scope of the present invention. Many variations and additions are possible within the scope of the present invention.

FIG. 1 illustrates a block diagram of an implantable hearing prosthesis system 10. The system 10 illustrated includes three components: a remote control 12, a sound processor 14 and an implant 16. It will be appreciated that the illustrated system 10 is but one example and that the invention can be applied to a wide variety of system configurations with different numbers and types of components. As shown, each component includes a number of ICs which each provide different operating functionalities for the respective component in which the IC is installed.

The remote control 12 is illustrated as having a microcontroller IC 18 and a wireless transceiver IC 20. The same wireless transceiver IC 20 is also installed in the sound processor 14 and the implant 16. The sound processor 14 additionally includes a DSP IC 26. The same DSP IC 26 is also found in the implant 16. The implant additionally includes a stimulator IC 22 and an implantable battery 24.

Given that the same DSP IC 26 can be used in the sound processor 14 and the implant 16, these may be considered to be generic DSP ICs in respect of their architecture and functional capabilities. However, in the present embodiment, the required functionality of the sound processor 14 DSP IC 26 will be different from the required functionality of the implant 16 DSP IC 26. In this regard, each DSP IC 26 will utilize different operating setting and parameters to function appropriately in its respective component.

FIG. 2 illustrates a block diagram of a typical processor-type IC 200, e.g. a DSP or microcontroller.

In FIG. 3, the processor-type IC 200 is installed in both an external 210 and an internal 212 part of a prosthesis system 204. The processor IC 200 needs to change its behavior or functionality depending upon which component it is installed in. As a basic example, the processor IC 200 needs to functionally communicate over a UART interface 206 with a programming system 208 when it is used in the external part 210, but it needs to functionally communicate over a wireless RF interface 214 when it is used in the internal part 212. Hence, while the processor ICs 200 are architecturally the same, in normal operation they are required to provide different functionalities based on the respective components in which each is installed.

The generic processor ICs 200 can be configured to provide their individually required functionality during initialization of the system 204. At startup the processor 200 loads a boot loader (or initialization) program and starts executing the boot loader program. The boot loader program causes a processor program to be downloaded from non-volatile memory (e.g. ROM) into the processor memory 220 (RAM). The functionality of the boot loader program (and also of the IC 200) needs to be different depending upon in which component the IC 200 is installed. Therefore, the IC 200 needs to determine where it has been installed. The boot loader program can do this by checking at start-up time how one or more of the ICs connecting pins have been electrically connected during installation, see FIG. 4. The manner in which ICs are electrically connected via their pins during installation is different depending upon in which component the IC 200 is installed and/or the intended functionality of the installed IC 200. Hence, by determining the actual pin connection, the required functionality of the IC 200 during normal operation of the system can be readily determined by the boot loader. In the example shown in FIG. 4, pin1 401 is connected to supply rail (Vdd) 410 while pin2 402 and pin4 404 are connected to ground rail (Vss) 420. An example flow chart of the boot loader operation is illustrated in FIG. 5. At 510, it is determined whether pint 401 of the IC 200 is connected to: supply rail (Vdd) 410. If yes, then at 520 it is realized that the IC 200 is being used in an internal component which requires functionality that can be provided by executing code routine A (at 530). If it is determined that pin1 401 of the IC 200 is not connected to supply rail (Vdd) 410, then at 540 it is realized that the IC 200 is being used in an external component. In the example shown, further pin connections are required to be determined before the required functionality can be realized. Hence, at 550, it is determined whether pin2 402 is connected to supply rail (Vdd) 410. If yes, then the required functionality is determined to be provided by executing code routine B (at 560). If the determination is negative, then the required functionality is determined to be provided by executing code routine C (at 570). Following this example boot loader operation, the IC shown in FIG. 4, would be determined to be installed in an internal component requiring code routine A.

The ICs ROM could be installed with all of the potential functionality programs in place, whereby the initialization process causes a selection of the required program for future normal operations. Conceivably, however, the required functionality program could be downloaded from an external source during the initialization process thereby obviating the need for the IC ROM to have all potential programs.

While the present invention has been described with respect to specific embodiments, it will be appreciated that various modifications and changes could be made without departing from the scope of the invention. For example, during start up, the IC could communicate with an external source (e.g. a memory, another IC, or PC system) and the external source determines the required functionality of the IC. As a further example, while the foregoing contemplated a software solution it is envisaged that a hardware solution could be employed. In such a hardware example, the ICs functionality would not be programmable but fixed in hardware (hard-wired). In which case, the required functionality is not determined by a boot loader or a downloaded processor program that is executed from memory, but by a pre-programmed state machine in hardware.

The invention claimed is:

1. An electronic system including a plurality of components, each component including one or more integrated circuits, wherein each integrated circuit is, during normal operation of the system, configured in provide individual operating functionality for its respective component;
  wherein at least one of the integrated circuits is configured to be installed as a generic integrated circuit having a plurality of connecting pins and being capable of providing any one of a number of individual operating functionalities, the generic integrated circuit being configured to:
    determine where in the system the generic integrated circuit has been installed upon system initialization by determining which of the plurality of connecting pins have been electrically connected during installation and which one of the pins has been connected to a power supply during installation;
    based upon the determination, configure itself;
      to provide the individual operating functionality for normal operation of the system;
      as an internal part of the system in response to determining that a first one of the pins has been connected to the power supply; and
      as an external part of the system in response to determining that a second one of the pins has been connected to the power supply.

2. The system of claim 1, wherein the generic integrated circuit is further configured to, upon system initialization, execute an initialization program which allows the generic integrated circuit to detect one or more of where in the system the generic integrated circuit has been installed and which of the plurality of components the generic integrated circuit has been installed in.

3. The system of claim 1, wherein the generic integrated circuit is configured to, upon determining where in the system it has been installed, download a required operating program from an external source, the required operating program, upon execution by the generic integrated circuit, providing the individual operating functionality.

4. The system of claim 1, wherein the system is a hearing prosthesis system.

5. The system of claim 4, wherein at least one of the plurality of components is incorporated into an implantable part of the hearing prosthesis system.

6. The system of claim 5, wherein the hearing prosthesis system is a cochlear implant system.

7. A method for configuring the operating functionality of an electronic system, the system including a plurality of components, each component including one or more integrated circuits having a plurality of pins, wherein:
  during normal operation of the system, each integrated circuit provides individual operating functionality for its respective component; and
  at least one of the integrated circuits is installed as a generic integrated circuit capable of providing any one of a number of individual operating functionalities, the method comprising:
    determining, by the generic integrated circuit, where in the system the generic integrated circuit has been installed by determining which of the generic integrated circuit's plurality of pins have been electrically connected during installation and which one of the pins has been connected to a power supply during installation; and
    based upon the determining, the generic integrated circuit configuring itself;
      to provide the required individual operating functionality for normal operation of the system;
      as an internal part of the system in response to determining that a first one of the pins has been connected to the power supply; and
      as an external part of the system in response to determining that a second one of the pins has been connected to the power supply.

8. The method of claim 7, further comprising:
  the generic integrated circuit executing an initialization program that allows the generic integrated circuit to detect one or more of where in the system the generic integrated circuit has been installed and which of the plurality of components the generic integrated circuit has been installed in.

9. The method of claim 7, wherein the configuring comprises:
  the generic integrated circuit downloading a required operating program from an external source, the required operating program, upon execution by the generic integrated circuit, providing the required individual operating functionality.

10. The method of claim 7, wherein the system is a hearing prosthesis system.

11. The method of claim 10, wherein at least one of the plurality of components is incorporated into an implantable part of the hearing prosthesis system.

12. The method of claim 11, wherein the hearing prosthesis system is a cochlear implant system.

13. The system of claim 6, wherein the generic integrated circuit is configured for use in either an internal or external part of the cochlear implant system.

14. The system of claim 13, wherein the generic integrated circuit is configured to configure itself to provide communication functionality for either communicating over a UART interface if the generic integrated circuit determines that a first set of one or more of the plurality of connecting pins are connected or communicating over a wireless interface if the generic integrated circuit determines that a second set of one or more of the plurality of connecting pins are connected.

15. The method of claim 12, wherein the generic integrated circuit is configured for use in either an internal or external part of the cochlear implant system.

16. The method of claim 15, wherein the generic integrated circuit configuring itself to provide the required individual operating functionality for normal operation of the system comprises:
  the generic integrated circuit configuring itself to provide communication functionality for either communicating over a UART interface if the generic integrated circuit determines that a first set of one or more of the plurality of pins are connected, or communicating over a wireless interface if the generic integrated circuit determines that a second set of one or more of the plurality of pins are connected.

17. The system of claim 1, wherein during installation, a first one of the plurality of connecting, pins is connected to the power supply and other ones of the plurality of connecting pins are not connected to the power supply such that power is supplied in a mutually exclusive manner to the first one of the plurality of connecting pins.

18. The system of claim 1, wherein:
the system is a hearing prosthesis system;
an electrical connection of the first one of the plurality of connecting pins to the power supply causes the generic integrated circuit to configure as an internal part of the hearing prosthesis system; and
an electrical connection of the second one of the plurality of connecting pins causes the generic integrated circuit to configure as an external part of the hearing prosthesis system.

19. A hearing prosthesis system including a plurality of components, each component including one or more integrated circuits, wherein each integrated circuit is, during normal operation of the hearing prosthesis system, configured to provide individual operating functionality for its respective component;
wherein at least one of the integrated circuits is configured to be installed as a generic integrated circuit having a plurality of connecting pins and being capable of providing any one of a number of individual operating functionalities, the generic integrated circuit being configured to:
determine where in the hearing prosthesis system the generic integrated circuit has been installed upon initialization of the hearing prosthesis system by determining which of the plurality of connecting pins have been electrically connected during installation and which one of the pins has been connected to a power supply during installation;
based on the determination, configure itself:
to provide the individual operating functionality;
as an internal part of the hearing prosthesis system in response to the generic integrated circuit determining that a first one of the pins has been connected to the power supply; and
as an external part of the hearing prosthesis system in response to the generic integrated circuit determining that a second one of the pins has been connected to the power supply.

* * * * *